United States Patent [19]

Fuess

[11] Patent Number: Plant 7,725

[45] Date of Patent: Nov. 26, 1991

[54] CHRYSANTHEMUM PLANT NAMED FORT KNOX

[76] Inventor: Janet S. Fuess, 9011 Red Hill Rd., New Hartford, N.Y. 13413

[21] Appl. No.: 543,382

[22] Filed: Jun. 26, 1990

[51] Int. Cl.[5] ..... A01H 5/00

[52] U.S. Cl. ..... Plt./78

[58] Field of Search ..... Plt./78, 82.2

[56] References Cited

U.S. PATENT DOCUMENTS

P.P. 4,586 7/1980 Meek et al. ..... Plt. 78

P.P. 5,661 2/1986 Meek et al. ..... Plt. 78

P.P. 6,404 11/1988 Mack et al. ..... Plt. 78

P.P. 6,621 2/1989 Mack et al. ..... Plt. 78

*Primary Examiner*—Howard J. Locker

*Attorney, Agent, or Firm*—Foley & Lardner

[57] ABSTRACT

A Chrysanthemum plant named Fort Knox particularly characterized by its bright yellow ray floret color, almost fully double flowers, shatter-resistant flowers, seven week flower response in photoperiodic programs, vigorous and uniform growth habit, and its early natural flowering season in outdoor programs.

1 Drawing Sheet

The present invention comprises a new and distinct cultivar of Chrysanthemum, botanically known as *Dendranthema grandiflora,* and referred to by the cultivar name Fort Knox.

Fort Knox is a product of a planned breeding program which had the objective of creating new chrysanthemum cultivars with a freely branching, compact cushion habit, early flower response, brilliant golden yellow decorative flowers, and adaptability for production as a garden variety as well as a variety grown under photoperiodic control. Such traits in combination were not present in previously available commercial cultivars.

Fort Knox was originated from a hybridization made in a controlled breeding program in New Hartford, N.Y. in September 1987. The female parent was a yellow daisy identified as C87-103, and the male parent was a bronze decorative identified as A86-52.

Fort Knox was discovered and selected as one flowering plant within the progeny of the cross by applicant in August 1988 in a controlled environment in New Hartford, N.Y.

The first act of asexual reproduction of Fort Knox was accomplished when vegetative cuttings were taken from the initial selection in November 1988 in a controlled environment in New Hartford, N.Y., by technicians working under formulations established and supervised by applicant.

Horticultural examination of selected units initiated in August 1989 has demonstrated that the unique combination of characteristics as herein disclosed for Fort Knox are firmly fixed and are retained through successive generations of asexual reproduction.

Fort Knox has not been observed under all possible environmental conditions. The phenotype may vary significantly with variations in environment such as temperature, light intensity and daylength. The following observations, measurements and comparisons describe plants grown in Carpinteria, Calif. under greenhouse conditions which approximate those generally used in commercial greenhouse practice.

The following traits have been repeatedly observed and are determined to be basic characteristics of Fort Knox which, in combination, distinguish this Chrysanthemum as a new and distinct cultivar:

1. Bright yellow ray floret color.
2. Almost fully double flowers; only 32 disc florets present.
3. Flowers very resistant to shattering.
4. Fully expanded ray florets approximately 2.3 cm. long and 0.8 cm. wide.
5. Average of 185 ray florets per flower.
6. Capitulum 5 cm. in diameter.
7. Seven week flower response in greenhouse culture.
8. Performs well in the outdoor garden, flowering early in natural season.
9. Compact cushion habit, making it suitable for production in 4"-8" containers.
10. Freely branching and flowering.

Of the many commercial cultivars known to the present inventor, the most similar in comparison to Fort Knox is Goldmine, disclosed in U.S. Plant Pat. No. 5,661. In comparison to Goldmine, Fort Knox has a more brilliant yellow ray floret color (Goldmine is more of a yellow-gold), a larger capitulum diameter, and a more uniform mounding habit. Also, the natural season flowering date of Fort Knox is September 18 in New Hartford, N.Y., ten days earlier than Goldmine when grown in the same location. The decorative capitulum type and seven week response in photoperiodically controlled programs are similar to those same characteristics of Goldmine.

The accompanying photographic drawing shows typical inflorescence and foliage characteristics of Fort Knox, with colors being as nearly true as possible with illustrations of this type. The photograph is a relatively closeup view of the new cultivar, clearly showing the flower color, shape and form.

In the following description color references are made to The Royal Horticultural Society Colour Chart. The color values were determined between 1:00 and 3:00 p.m. on Mar. 14, 1990 under 4,000 foot candles at Carpinteria, Calif.

Classification:

*Botanical.*—*Dendranthema grandiflora* cv Fort Knox.

*Commercial.*—Garden mum and decorative spray pot mum.

INFLORESCENCE

A. Capitulum:

*Form.*—Generally flat.

*Type.*—Decorative.

*Diameter across face.*—5 cm.

B. Corolla of ray florets: 185 florets.

*Color (general tonality from a distance of three meters).*—Bright yellow, 9A.

*Color (lower surface).*—7B.

*Color (upper surface).*—9A.

*Size.*—2.3 cm. long and 0.8 cm. wide; irregular dentate tips.

C. Corolla of disc florets: 32 florets.

*Color (mature).*—7A.

*Color (immature).*—5A.

*Size.*—0.4 cm. long and 0.1 cm. wide; tubular; 5 pointed; cleistogamous-selfing without opening.

D. Reproductive organs:

*Androecium.*—Present on disc florets only; 5 stamens, 0.3 cm.; filaments separate; anther sacs connected and completely enclosing stigma.

*Gynoecium.*—Ray: Style, 0.6 cm.; 2–3 parted. Disc: Style, 0.2 cm.; bifurcated; enclosed in anther ring.

PLANT

A. General appearance:

*Height.*—25–35 cm. when grown in an 8″ container.

B. Foliage:

*Color (lower surface).*—147B.

*Color (upper surface).*—147A.

*Size.*—5–7 cm. long and 4–5 cm. wide.

*Shape.*—5 lobed with pronounced sinus and slightly acuminate tips.

I claim:

1. A new and distinct cultivar of Chrysanthemum plant named Fort Knox, as described and illustrated.

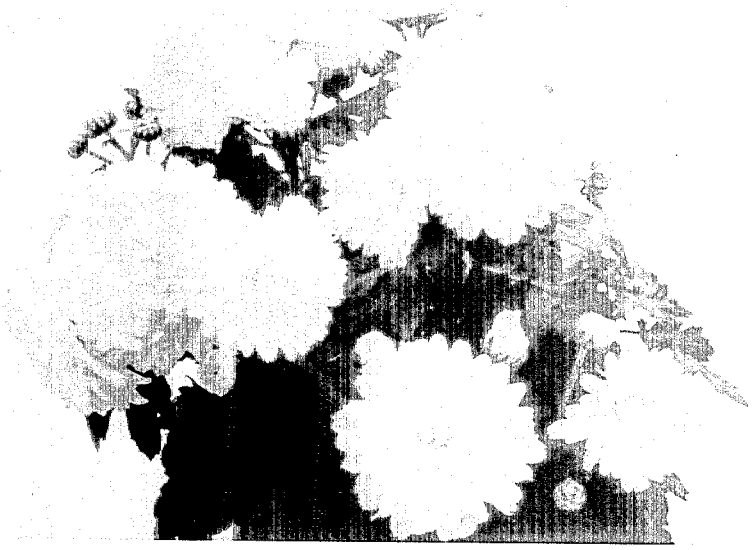

* * * * *